US00PP24903P2

(12) United States Plant Patent
Warren et al.

(10) Patent No.: US PP24,903 P2
(45) Date of Patent: Sep. 16, 2014

(54) CALLA LILY PLANT NAMED 'HOT BUTTER BLZ'

(50) Latin Name: ***Zantedeschia* spp.**
Varietal Denomination: Hot Butter BLZ

(71) Applicants: Andrew Geoffrey Fiennes Warren, Tauranga (NZ); Jacobus Petrus Spaans, Tauranga (NZ)

(72) Inventors: Andrew Geoffrey Fiennes Warren, Tauranga (NZ); Jacobus Petrus Spaans, Tauranga (NZ)

( * ) Notice: Subject to any disclaimer, the term of this patent is extended or adjusted under 35 U.S.C. 154(b) by 0 days.

(21) Appl. No.: 13/986,144

(22) Filed: Apr. 5, 2013

(51) Int. Cl.
*A01H 5/00* (2006.01)

(52) U.S. Cl.
USPC ..... Plt./490

(58) Field of Classification Search
USPC ..... Plt./490
See application file for complete search history.

*Primary Examiner* — June Hwu
*Assistant Examiner* — Keith Robinson

(57) ABSTRACT

A calla lily plant particularly distinguished by cream spathes, light maculation of the leaves that is visible from both sides, visible venation of the leaves in early growth stage and early flowering producing 4 to 6 inflorescences per 3-cm tuber, is described.

3 Drawing Sheets

Genus and species: *Zantedeschia* spp.
Variety denomination: 'Hot Butter BLZ'.

BACKGROUND OF THE NEW PLANT

The present invention comprises a new and distinct cultivar of calla lily, botanically known as *Zantedeschia* spp., and hereinafter referred to by the cultivar name 'Hot Butter BLZ'. The new cultivar was asexually reproduced by tissue culture resulting from the cross of the female parent an unnamed, unpatented *Zantedeschia* variety having cream spathes and the male parent 'Pink Pot' (U.S. Pat. No. 14,531) *Zantedeschia* variety having pink spathes. 'Hot Butter BLZ' is a product of a planned breeding program intended to create new calla lily plants with cream spathes.

The new cultivar was created in Tauranga, New Zealand and has been asexually reproduced repeatedly by tissue culture in Bangalore, India over a two year period. The present invention has been found to retain its distinctive characteristics through successive propagations.

Plant Breeder's Rights for this cultivar were applied for in New Zealand on Aug. 28, 2012. 'Hot Butter BLZ' has not been made publicly available anywhere in the world more than one year prior to the filing date of this application.

SUMMARY OF THE INVENTION

The following are the most outstanding and distinguishing characteristics of this new cultivar when grown under normal horticultural practices in Tauranga, New Zealand.

1. Cream spathes
2. Light maculation of the leaves that is visible from both sides
3. Visible venation of the leaves in early growth stage
4. Early flowering
5. Produces 4 to 6 inflorescences per 3-cm tuber.

DESCRIPTION OF THE PHOTOGRAPHS

This new calla lily plant is illustrated by the accompanying photographs which show the plant habit, mature inflorescence and foliage of the plant. The colors shown are as true as can be reasonably obtained by conventional photographic procedures. The photographs are of a plant approximately 8 weeks old, after planting in optimum conditions.

DESCRIPTION OF THE NEW CULTIVAR

Figure 1:
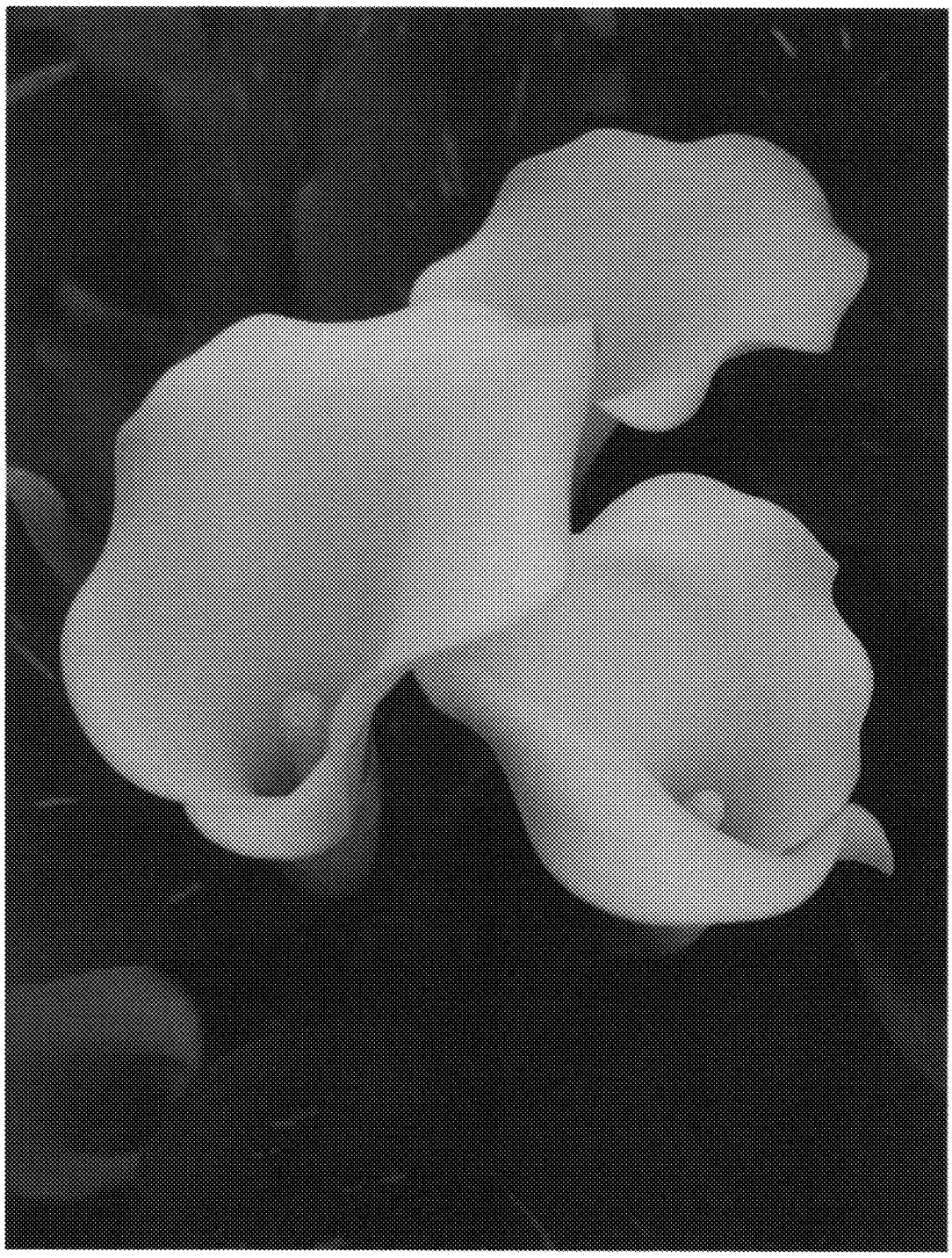
FIG. 1 shows a close-up of mature inflorescences.
Figure 2:
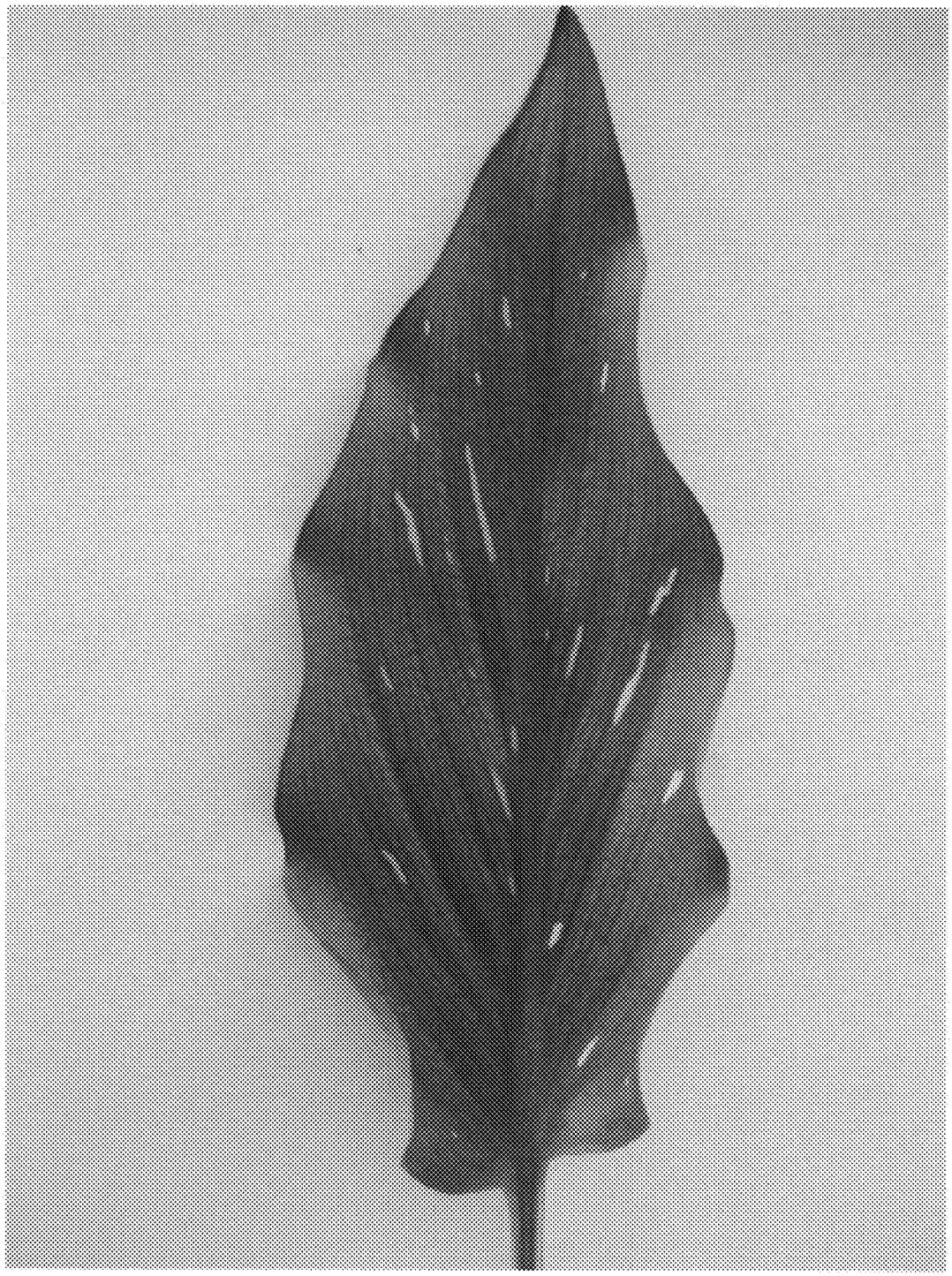
FIG. 2 shows a close-up of the leaf venation and maculation.
Figure 3:
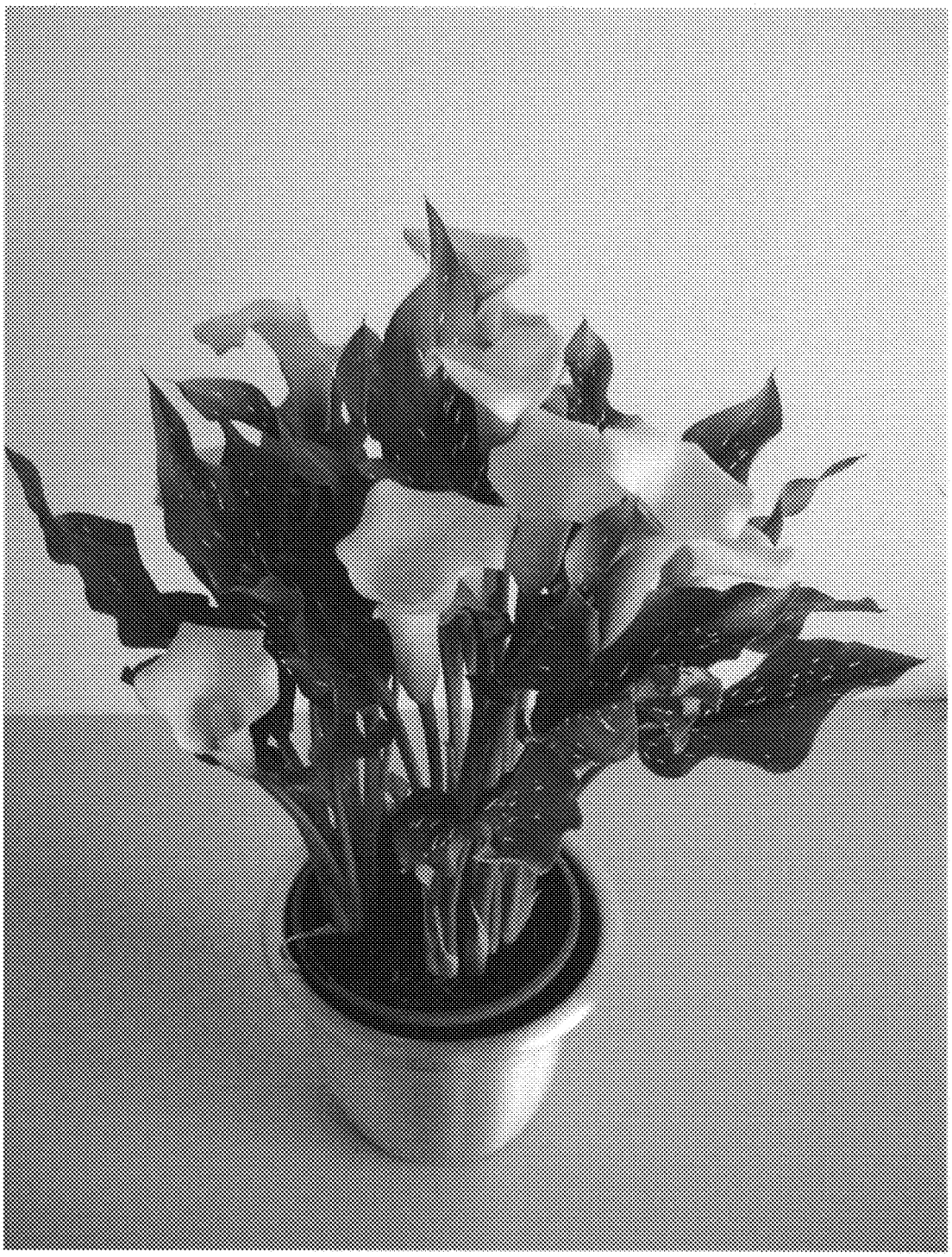
FIG. 3 shows the mature inflorescence and foliage.

The following detailed description sets forth the distinctive characteristics of 'Hot Butter BLZ'. The data that define these characteristics were collected from asexual reproductions carried out in New Zealand. The plant history was taken on plants of two-year-old tubers based on a 3-cm diameter tuber under New Zealand summer conditions. Color references are primarily to the 1995 edition of The Colour Chart of The Royal Horticultural Society of London (R.H.S.).

DETAILED BOTANICAL DESCRIPTION

Classification:
- *Family.*—Araceae.
- *Botanical name.*—*Zantedeschia* spp.
- *Common name.*—Calla lily.

Parentage:
- *Female parent.*—An unnamed, unpatented *Zantedeschia* variety having cream spathes.
- *Male parent.*—'Pink Pot' (U.S. Pat. No. 14,531) *Zantedeschia* variety having pink spathes.

Plant:
- *Form.*—Erect.
- *Height of the leaf canopy above the soil.*—35 cm to 55 cm.
- *Height of top of inflorescence above the soil.*—20 cm to 40 cm.
- *Diameter.*—30 cm to 40 cm.

*Number of inflorescences per tuber size*.—Tuber diameter 3 cm: 4 to 6. Tuber diameter 4 cm: 6 to 12. Tuber diameter 5 cm: 10+.

*Time to produce a finished flowering plant*.—5 to 8 weeks depending on the climate and environment.

*Lastingness of the inflorescence on the plant*.—2 to 4 weeks.

Growing points:

*Character*.—Strong.

*Color*.—Upper: RHS 144A. Lower: RHS 144B. Base: RHS 144B.

*Average number*.—3 to 8.

Leaves:

*Size*.—Length: 15 cm to 22 cm. Width: 8 cm to 11 cm.

*Shape*.—Lanceolate.

*Apex*.—Narrowly Acute.

*Base*.—Attenuate.

*Margin*.—Entire.

*Margin color*.—RHS146B.

*Venation pattern*.—Pinnate, very distinct in early leaf growth.

*Surface texture*.—Leathery.

*Color*.—Upper surface: RHS 146A. Lower surface: RHS 147B.

*Maculation* (*leaf spots*).—General: Maculation is only on the upper surface of the leaf but is visible from the lower surface. Density: Light density. Color: RHS 157A.

*Petiole*.—Average number per tuber: 9 to 14. Length: 12 cm to 23 cm. Diameter: 0.4 cm to 0.6 cm. Texture: Smooth. Character: Strong. Shape: Slightly flattened. Color: Base: RHS 146B. Upper portion: RHS 146B. Sheath: Length: 4 cm to 8 cm. Diameter: 0.8 cm to 1 cm. Color: RHS 146B.

Roots:

*Color*.—RHS 155D (white).

*Branching*.—Not branched, attached to the top of the tuber at the apices.

Inflorescence:

*Spathe* (*flower body*).—Size: Length: 7.5 cm to 9 cm. Width: 5.5 cm to 6.5 cm. Height: 8 cm to 10 cm. Color: Upper portion: RHS 3D. Lower portion: RHS 3C. Outer surface of the base: some green coloration RHS 146D. Fading: does not fade. Vein color: RHS 3D. Fragrance: Absent. Shape: Round. Texture: Smooth. Apex: Apiculate. Base: Attenuate. Margin: Undulate. Size of throat spot: small. Colour of throat spot: RHS 59B.

*Spadix* (*reproductive organs*).—Size: Length: 3 cm to 4.5 cm. Diameter: 0.7 cm to 0.9 cm. Color: Base: RHS 145B. Upper part: RHS 145B. Position relative to spathe: Upright. Shape: Elongated. Apex: Rounded.

*Peduncle* (*flower stem*).—Length: 20 cm to 40 cm. Diameter: 0.6 cm to 0.8 cm. Color: Base: RHS 146B, mottled with RHS 146D. Upper part: RHS 146B. Surface texture: Smooth. Strength: Strong.

Reproductive organs:

*Location of female organs*.—Basal position of the spadix.

*Location of male organs*.—Upper position of the spadix.

*Perianth* (*the floral envelope, calyx and corolla*).—Conspicuous.

*Pollen color*.—RHS 155D (white).

*Stamens*.—Not visible before pollen release.

*Pistil*.—Number: 30 to 45 per spadix. Color: RHS 6A.

Fruit (berries):

*Quantity of berries per plant*.—30 to 45.

*Color*.—RHS 144B.

*Size*.—Length: 3.5 cm to 4.5 cm (whole fruit). Width: 2.5 cm to 3 cm (whole fruit). Diameter: 0.5 cm to 0.8 cm (individual berry).

Disease and insect resistance:

*Disease resistance*.—No susceptibility to date.

*Pest resistance*.—No susceptibility to date.

COMPARISON WITH PARENTAL AND KNOWN CULTIVARS

When compared to the commercial variety 'Pot of Gold' (unpatented), 'Hot Butter BLZ' has a less dense leaf maculation pattern, distinct leaf venation in early growth, a greater number of inflorescences, cream spathe colour and shorter plant height.

When compared to the commercial variety 'Yellow Jacket BLZ' (U.S. Plant Pat. No. 20,217), 'Hot Butter BLZ' has a less dense leaf maculation pattern, distinct leaf venation in early growth, presence of throat spot and cream spathe colour.

When compared to the female parent 'Hot Butter BLZ' has distinct leaf venation in early growth, a greater number of inflorescences and stronger peduncles (flower stems).

When compared to the male parent 'Hot Butter BLZ' has a more dense leaf maculation pattern, distinct leaf venation in early growth, a greater number of inflorescences, stronger peduncles (flower stems) and cream spathe colour.

We claim:

1. A new and distinct cultivar of calla lily plant as shown and described herein.

* * * * *